USO12172008B2

(12) United States Patent
Herbst et al.

(10) Patent No.: US 12,172,008 B2
(45) Date of Patent: *Dec. 24, 2024

(54) METHODS FOR PRODUCING CARDIOMYOCYTE CELLS

(71) Applicant: Boston Scientific Scimed Inc., Maple Grove, MN (US)

(72) Inventors: Thomas J. Herbst, Coon Rapids, MN (US); Craig Stolen, New Brighton, MN (US)

(73) Assignee: Boston Scientific Seimed, Inc., Maple Grove, MN (US)

( * ) Notice: Subject to any disclaimer, the term of this patent is extended or adjusted under 35 U.S.C. 154(b) by 397 days.

This patent is subject to a terminal disclaimer.

(21) Appl. No.: 17/404,768

(22) Filed: Aug. 17, 2021

(65) Prior Publication Data

US 2021/0370057 A1 Dec. 2, 2021
US 2024/0335658 A9 Oct. 10, 2024

Related U.S. Application Data

(63) Continuation of application No. 16/148,838, filed on Oct. 1, 2018, now Pat. No. 11,116,969, which is a
(Continued)

(51) Int. Cl.
*A61N 1/32* (2006.01)
*A61N 1/05* (2006.01)
(Continued)

(52) U.S. Cl.
CPC ............. *A61N 1/326* (2013.01); *A61N 1/056* (2013.01); *A61N 1/0573* (2013.01); *A61N 1/205* (2013.01);
(Continued)

(58) Field of Classification Search
CPC ...... A61N 1/326; A61N 1/056; A61N 1/0573; A61N 1/205; A61N 1/3628; A61N 1/3756; C12N 5/0657
See application file for complete search history.

(56) References Cited

U.S. PATENT DOCUMENTS 3,902,501 A * 9/1975 Citron ................... A61N 1/057
607/126
5,632,716 A 5/1997 Bui et al.
(Continued)

FOREIGN PATENT DOCUMENTS

EP 1827577 B1 9/2008
JP 2007-526021 A 9/2007
(Continued)

OTHER PUBLICATIONS

"Ingevity MRI Pacing Lead," Boston Scientific, 5 pp. 2016.
(Continued)

*Primary Examiner* — Eugene T Wu
(74) *Attorney, Agent, or Firm* — Pauly, DeVries Smith & Deffner LLC

(57) ABSTRACT

A method for producing cardiomyocyte cells including implanting a substrate within a heart such that a first portion of the substrate is in physical contact with an endocardium and a second portion of the substrate is not in contact with the endocardium, maintaining the first portion of the substrate in contact with the endocardium for a time at least sufficient to form trabecular fibers extending between the endocardium and the second portion of the substrate, cutting away the trabecular fibers from the endocardium, cutting away the trabecular fibers from the substrate, and removing the trabecular fibers from the heart, wherein the trabecular fibers include cardiomyocyte cells.

9 Claims, 7 Drawing Sheets

Related U.S. Application Data continuation of application No. 15/239,565, filed on Aug. 17, 2016, now Pat. No. 10,118,034.

(60) Provisional application No. 62/206,845, filed on Aug. 18, 2015.

(51) Int. Cl.
  *A61N 1/20* (2006.01)
  *A61N 1/362* (2006.01)
  *A61N 1/375* (2006.01)
  *C12N 5/077* (2010.01)

(52) U.S. Cl.
  CPC ......... *A61N 1/3628* (2013.01); *A61N 1/3756* (2013.01); *C12N 5/0657* (2013.01)

(56) References Cited

U.S. PATENT DOCUMENTS

| | | | |
|---|---|---|---|
| 10,118,034 B2* | 11/2018 | Herbst | A61N 1/3628 |
| 10,773,077 B2 | 9/2020 | Herbst et al. | |
| 11,116,969 B2 | 9/2021 | Herbst et al. | |
| 2003/0134282 A1* | 7/2003 | Bristow | C07K 14/4716 |
| | | | 435/6.12 |
| 2004/0186546 A1 | 9/2004 | Mandrusov et al. | |
| 2005/0113900 A1* | 5/2005 | Shiroff | A61B 17/0469 |
| | | | 607/130 |
| 2005/0154252 A1 | 7/2005 | Sharkey et al. | |
| 2006/0129216 A1 | 6/2006 | Hastings et al. | |
| 2007/0106201 A1 | 5/2007 | Soykan et al. | |
| 2009/0062894 A1 | 3/2009 | Stahmann et al. | |
| 2011/0082538 A1 | 4/2011 | Dahlgren et al. | |
| 2011/0237967 A1 | 9/2011 | Moore et al. | |
| 2012/0251508 A1 | 10/2012 | Basu et al. | |
| 2013/0231727 A1 | 9/2013 | Carlson et al. | |
| 2014/0296912 A1 | 10/2014 | Whitman et al. | |
| 2015/0088155 A1 | 3/2015 | Stahmann et al. | |
| 2015/0306381 A1 | 10/2015 | Schmidt et al. | |
| 2016/0186139 A1* | 6/2016 | Regnier | A61K 48/005 |
| | | | 435/325 |
| 2017/0050018 A1 | 2/2017 | Herbst et al. | |
| 2018/0147409 A1 | 5/2018 | Herbst et al. | |
| 2019/0030327 A1 | 1/2019 | Herbst et al. | |

FOREIGN PATENT DOCUMENTS

| | | |
|---|---|---|
| JP | 2008-516000 A | 5/2008 |
| WO | 01/28455 A1 | 4/2001 |
| WO | 2005/039691 A1 | 5/2005 |
| WO | 2017/031238 A2 | 2/2017 |
| WO | 2018/097884 A1 | 5/2018 |

OTHER PUBLICATIONS

Barile, Lucile, et al. "Human Cardiospheres as a Source of Multipotent Stem and Progenitor Cells." Stem Cells International, vol. 2013, Article ID 916837, 10 pages, Apr. 19, 2013.
Boston Scientific. "SpyGlass Direct Visualization System." Boston Scientific, 12 pages, Apr. 2013.
Cigna. "Cigna HealthCare Coverage Position: Partial Left Ventriculectomy Dynamic Cardiomyoplasty and Ventricular Reshaping in the Treatment of Heart Failure." Cigna, revised Mar. 15, 2006, 10 pages.
Grandjean, P. A., et al. "Long-Term Outcome of Dynamic Cardiomyoplasty in France." Basic Applied Myology, 19(1): 17-24, 2009.
International Search Report and Written Opinion issued in PCT/US2016/047413, dated Nov. 28, 2016, 7 pages.
International Search Report and Written Opinion issued in PCT/US2017/052909, dated Dec. 13, 2017, 14 pages.
International Search Report and Written Opinion issued in PCT/US2017/052909, mailed Dec. 13, 2017, 14 pages.
Makkar, Raj R., et al. "Intracoronary Cardiosphere-Derived Cells for Heart Regeneration After Myocardial Infarction (Caduceus): A Prospective, Randomised Phase 1 Trial." Lancet, 379:895-904, Mar. 10, 2012.
Messina, Elisa, et al. "Isolation and Expansion of Adult Cardiac Stem Cells From Human and Murine Heart." Cellular Biology, Circ. Res., 95:911-921 and Supplemental Material, 22 pages, 2004.
Smith, Rachel Ruckdeschel, et al. "Regenerative Potential of Cardiosphere-Derived Cells Expanded From Percutaneous Endomyocardial Biopsy Specimans." Circulation, 115:896-908, 2007.
Ye, Lei, et al. "Patching the Heart: Cardiac Repair From Within and Outside." Circulation Research, 113:922-932, 2013.
Zoler, Mitchel. "The Surgery Was a Success, but the Device Died." EGMN: Notes from the Road [online], Mar. 24, 2010, retrieved from https://egmnblog.wordpress.com/2010/03/24/the-surgery-was-a-success-but-the-device-died/, 3 pages.

* cited by examiner

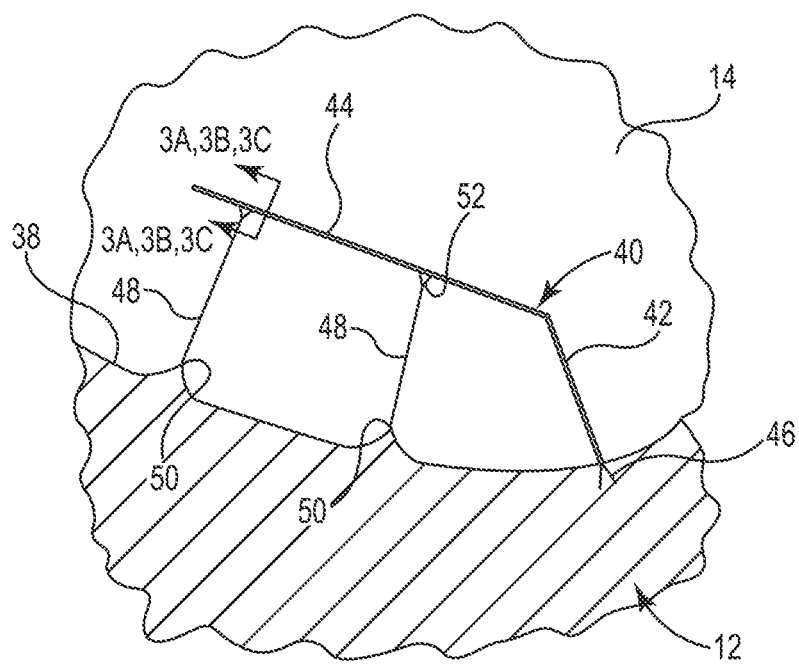
Fig. 2
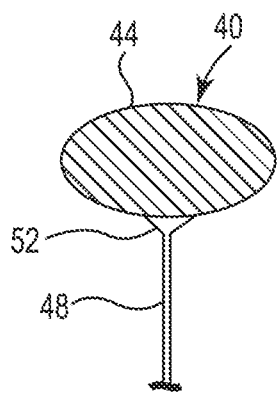 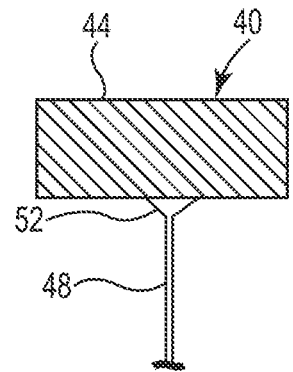 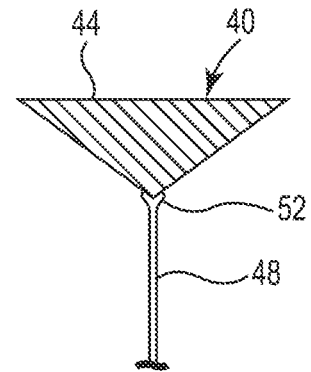
Fig. 3A  Fig. 3B  Fig. 3C

METHODS FOR PRODUCING CARDIOMYOCYTE CELLS

CROSS-REFERENCE TO RELATED APPLICATION

This application is a continuation of U.S. application Ser. No. 16/148,838, filed Oct. 1, 2018, which is a continuation of U.S. application Ser. No. 15/239,565, filed Aug. 17, 2016, now U.S. Pat. No. 10,118,034, issued Nov. 6, 2018, which claims priority to Provisional Application No. 62/206,845, filed Aug. 18, 2015, which is herein incorporated by reference in its entirety.

TECHNICAL FIELD

The present invention relates to methods for stimulating the growth of new muscle cells and tissue. More specifically, the invention relates to stimulating the growth of new contractile heart muscle cells and cardiac tissue.

BACKGROUND

Millions of people suffer from a weakened or damaged heart resulting in impaired cardiac output. One method for treating a weakened or damaged heart is by dynamic cardiomyoplasty. In dynamic cardiomyoplasty, a flap of a latissimus dorsi skeletal muscle is moved into the chest and wrapped around failing heart ventricles. The muscle flap is electrically stimulated in concert with the contraction of the ventricles to assist with the contraction of the heart and improve cardiac output.

The use of a skeletal muscle, such as the latissimus dorsi, is not ideal for cardiac applications because of inherent differences between skeletal muscle tissue and cardiac muscle tissue. For example, skeletal muscle tissue fatigues quickly while cardiac muscle tissue does not.

SUMMARY

Example 1 is a method for producing cardiomyocyte cells including implanting a substrate within a heart such that a first portion of the substrate is in physical contact with an endocardium and a second portion of the substrate is not in contact with the endocardium, maintaining the first portion of the substrate in contact with the endocardium for a time at least sufficient to form trabecular fibers extending between the endocardium and the second portion of the substrate, cutting away the trabecular fibers from the endocardium, cutting away the trabecular fibers from the substrate, and removing the trabecular fibers from the heart, wherein the trabecular fibers include cardiomyocyte cells.

In Example 2, the method of Example 1, wherein the substrate is implanted within a right ventricle of the heart.

In Example 3, the method of any of Examples 1-2, wherein the substrate includes a biocompatible polymer.

In Example 4, the method of Example 3, wherein the biocompatible polymer is selected from the group consisting of a polyurethane polymer, a polyether ether ketone polymer, and a silicone polymer.

In Example 5, the method of any of Examples 1-4, wherein the trabecular fibers are cut from the endocardium at a location where the trabecular fibers extend from the endocardium.

In Example 6, the method of any of Examples 1-5, wherein the trabecular fibers are cut from the substrate at a location where the trabecular fibers extend from the substrate.

In Example 7, the method of any of Examples 1-6, further including separating the first portion of the substrate from the endocardium after cutting away the trabecular fibers from the endocardium, and removing the substrate and the attached trabecular fibers from the heart before cutting away the trabecular fibers from the substrate.

In Example 8, the method of any of Examples 1-7, wherein the substrate is implanted percutaneously.

In Example 9, the method of any of Examples 1-8, wherein maintaining the first portion of the substrate in contact with the endocardium includes anchoring the substrate to the endocardium with a fixation device.

In Example 10, the method of any of Examples 1-6, wherein the substrate further includes an electrode, wherein the electrode is not in physical contact with the endocardium.

In Example 11, the method of Example 10, wherein maintaining includes anchoring the substrate to the endocardium with a fixation device, and producing an electrical potential between the electrode and the endocardium.

In Example 12, the method of Example 11, wherein the electrical potential is produced as a series of electrical pulses.

In Example 13, the method of Example 11, wherein the electrical potential is produced continuously.

In Example 14, the method of any of Examples 11-13, wherein the electrode includes a biocompatible electrical conductor.

In Example 15, the method of any of Examples 11-14, further including removing the substrate from the heart after removing the trabecular fibers containing the cardiomyocyte cells from the heart.

Example 16 is a method for producing cardiomyocyte cells including implanting a substrate within a heart such that a first portion of the substrate is in physical contact with an endocardium and a second portion of the substrate is not in contact with the endocardium, maintaining the first portion of the substrate in contact with the endocardium for a time at least sufficient to form trabecular fibers extending between the endocardium and the second portion of the substrate, cutting away the trabecular fibers from the endocardium, cutting away the trabecular fibers from the substrate, and removing the trabecular fibers from the heart, wherein the trabecular fibers include cardiomyocyte cells.

In Example 17, the method of Example 16, wherein the substrate is implanted percutaneously.

In Example 18, the method of any of either of Examples 16 or 17, wherein the substrate is implanted within a right ventricle of the heart.

In Example 19, the method of Examples 16-18, wherein the substrate includes a biocompatible polymer.

In Example 20, the method of Example 19, wherein the biocompatible polymer is selected from the group consisting of a polyurethane polymer, a polyether ether ketone polymer, and a silicone polymer.

In Example 21, the method of any of Examples 16-20, wherein the trabecular fibers are cut from the endocardium at a location where the trabecular fibers extend from the endocardium.

In Example 22, the method of any of Examples 16-21, wherein the trabecular fibers are cut from the substrate at a location where the trabecular fibers extend from the substrate.

Example 23 is a method for producing cardiomyocyte cells including implanting a substrate within a heart such that a first portion of the substrate is in physical contact with an endocardium and a second portion of the substrate is not in contact with the endocardium, maintaining the first portion of the substrate in contact with the endocardium for a time at least sufficient for trabecular fibers to form, the trabecular fibers extending between the endocardium and the second portion of the substrate, cutting away the trabecular fibers from the endocardium, separating the first portion of the substrate from the endocardium, and removing the substrate and the attached trabecular fibers from the heart, wherein the trabecular fibers include cardiomyocyte cells.

In Example 24, the method of Example 23, wherein the substrate is implanted within a right ventricle of the heart.

In Example 25, the method of either of Examples 23 or 24, wherein the substrate includes a biocompatible polymer.

In Example 26, the method of Example 25, wherein the biocompatible polymer is selected from the group consisting of a polyurethane polymer, a polyether ether ketone polymer, and a silicone polymer.

In Example 27, the method of any of Examples 23-26, wherein the trabecular fibers are cut from the endocardium at a location where the trabecular fibers extend from the endocardium.

Example 28 is a method for producing cardiomyocyte cells including positioning a substrate including an electrode within a heart such that the substrate is in physical contact with an endocardium and the electrode is not in physical contact with the endocardium, maintaining the substrate within the heart for a time at least sufficient to form trabecular fibers extending between the endocardium and the electrode, cutting away the trabecular fibers from the endocardium, cutting away the trabecular fibers from the electrode, and removing the trabecular fibers from the heart, wherein the trabecular fibers contain cardiomyocyte cells.

In Example 29, the method of Example 28, wherein maintaining includes anchoring the substrate to the endocardium with a fixation device, and producing an electrical potential between the electrode and the endocardium.

In Example 30, the method of either of Examples 28 or 29, wherein the electrical potential is produced as a series of electrical pulses.

In Example 31, the method of either of Examples 28-29, wherein the electrical potential is produced continuously.

In Example 32, the method of any of Examples 28-31, wherein the substrate includes a biocompatible polymer and the electrode includes a biocompatible electrical conductor.

In Example 33, the method of any of Examples 28-32, wherein the trabecular fibers are cut from the endocardium at a location where the trabecular fibers extend from the endocardium.

In Example 34, the method of any of Examples 28-33, wherein the trabecular fibers are cut from the substrate at a location where the trabecular fibers extend from the electrode.

In Example 35, the method of any of Examples 28-34, further including removing the substrate from the heart after removing the trabecular fibers containing the cardiomyocyte cells from the heart.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2 is a schematic view of a portion of the patient's heart further illustrating implanted substrate of FIG. 1.

FIGS. 3A-3C are schematic cross-sectional views illustrating exemplary cross-sectional shapes for the substrate of FIG. 2.

Figure 1:
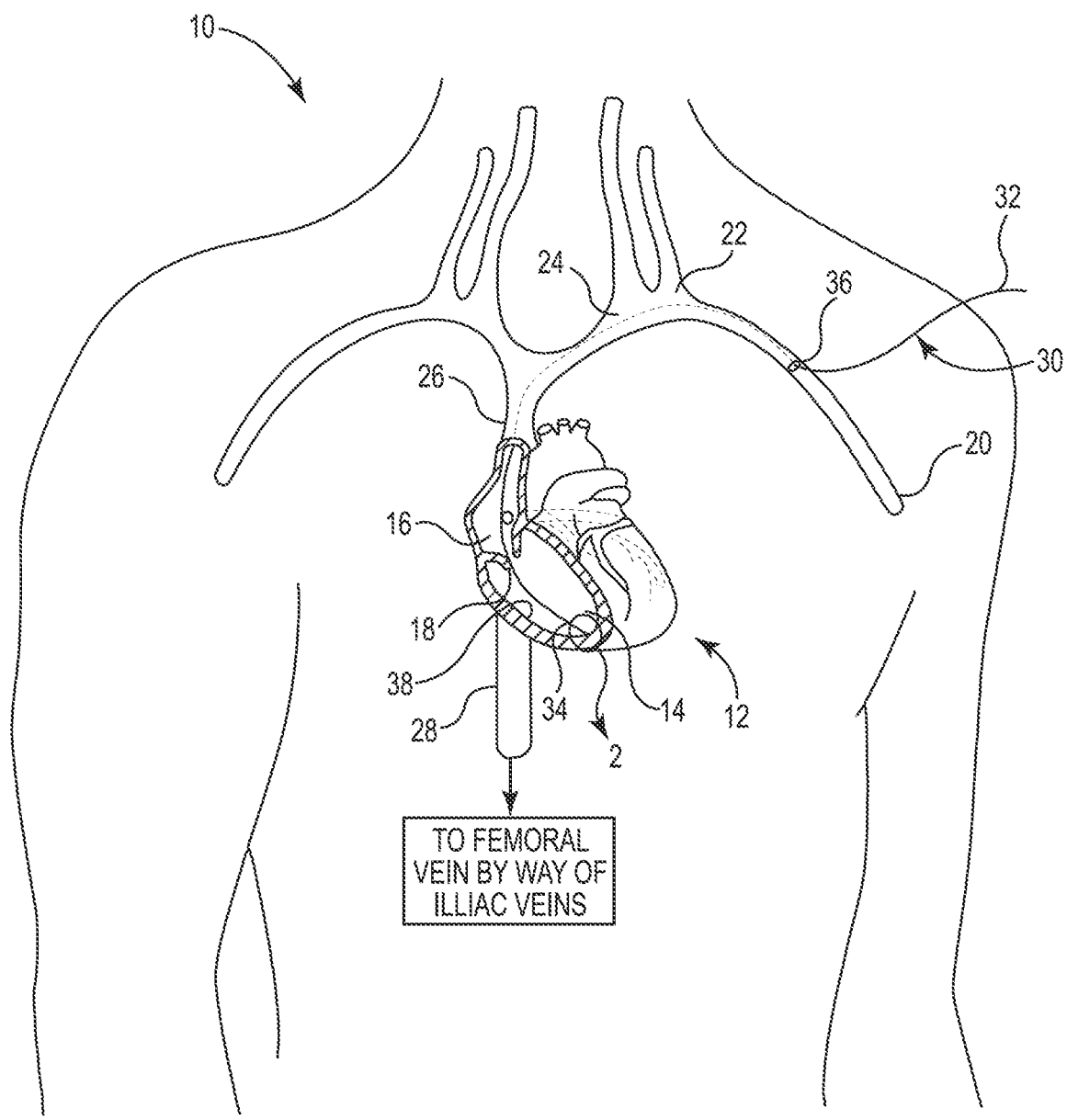
FIG. 1 is a schematic view illustrating the implantation of a substrate for stimulating the growth of new contractile heart muscle tissue, or cardiomyocyte cells, in accordance with embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view illustrating the implantation of a substrate for stimulating the growth of new contractile heart muscle tissue, or cardiomyocyte cells, in accordance with embodiments of the present invention. Cardiomyocyte cells produced and harvested as described below may be used for dynamic cardiomyoplasty. The use of the cardiomyocyte cells produced as described herein overcome the deficiencies inherent with using skeletal muscle tissue in cardiomyoplasty, such as fatigue, at least because the cardiomyocyte cells produced are cardiac muscle tissue, not skeletal muscle tissue.

The cardiomyocyte cells produced as described herein are new cardiomyocyte cells grown de novo within the heart chamber, and not pre-existing heart tissue. Without wishing to be bound by any theory, these de novo tissues may be derived from cardiac stem cell populations resident in the heart chamber, or from populations of pluripotent circulating stem cells. Such newly generated cardiomyocyte cells may be a source of ex vivo expanded cells for use in cardiac regeneration.

FIG. 1 is a schematic view illustrating the implantation of a substrate for stimulating the growth of new contractile heart muscle tissue, or cardiomyocyte cells. FIG. 1 illustrates a patient 10 including a heart 12. The heart 12 includes a right ventricle 14, a right atrium 16, and a tricuspid valve 18 separating the right atrium 16 from the right ventricle 14. Also shown in FIG. 1 are veins directing blood to the heart 12 including a left auxiliary vein 20, which flows into a left subclavian vein 22, which flows into a left brachiocephalic vein 24. The left brachiocephalic vein 24 flows into a superior vena cava 26, which supplies blood to the right atrium 16. An inferior vena cava 28 receives blood from a femoral artery (not shown) by way of an external iliac vein (not shown) and a common iliac vein (not shown). The inferior vena cava 28 also supplies blood to the right atrium 16.

FIG. 1 shows a catheter 30 having a proximal end 32 and a distal end 34. In some embodiments, the catheter 30 may enter the left auxiliary vein 20 percutaneously through a vascular entry site 36. The distal end 34 may be maneuvered through a left auxiliary vein 20, the left subclavian vein 22, the left brachiocephalic vein 24, the superior vena cava 26, and into the heart 12 at the right atrium 16. In other embodiments, the catheter 30 may percutaneously enter the femoral artery. The distal end 34 may be maneuvered through the external iliac vein, the common iliac vein, the inferior vena cava 28, and into the heart 12 at the right atrium 16. In either embodiment, the distal end 34 may be maneuvered from the right atrium 16, through the tricuspid valve 18, and into the right ventricle 14. The catheter 30 may include at least one lumen (not shown) extending from the proximal end 32 to the distal end 34 through which instruments (not shown) may be used to implant a substrate into an endocardium 38 lining the walls of the right ventricle 14, such as a substrate 40 for stimulating the growth of new cardiomyocyte cells as described below in reference to FIG. 2.

FIG. 2 is a schematic view illustrating the substrate 40 implanted into the endocardium 38 of the heart 12. FIG. 2 shows the substrate 40 includes a first portion 42, a second portion 44, and a fixation device 46. In various embodiments, the substrate 40 may be made at least in part from a biocompatible polymer, for example, a polyurethane polymer, a polyether ether ketone polymer, a silicone polymer, a styrene-isobutylene-styrene block copolymer, or an expanded polytetrafluoroethylene polymer. Alternatively, the substrate 40 may be made at least in part of an organic substance, for example, cellulose, fibrin, fibrinogen, or fibronectin. In one embodiment, the substrate 40 may be a solid or an e-spun mesh.

The fixation device 46 may be a passive fixation device, such as tines as illustrated in FIG. 2, or an active fixation device, such as a hook or helix. The fixation device 46 is connected to one end of the first portion 42 to anchor the substrate 40 to the endocardium 38. The second portion 44 is connected to the other end of the first portion 42 and is not in contact with the endocardium 38. That is, the second portion 44 of the substrate 40 is spaced apart from the endocardium 38. The first portion 42 may be maintained in contact with the endocardium 38 for a time at least sufficient for the formation of a trabecular fiber 48 extending between the endocardium 38 and the second portion 44, as shown in FIG. 2. In some embodiments, the trabecular fiber 48 may extend from the endocardium 38 at a location 50. In some embodiments, the endocardium 38 may be pulled toward the second portion 44 due to tension transmitted along the trabecular fiber 48 between the endocardium 38 and the substrate 40. In some embodiments, the trabecular fiber 48 may extend from the substrate 40 at a location 52.

For clarity of illustration, all embodiments herein are shown producing two trabecular fibers 48. It is understood that embodiments may have as few as one trabecular fiber 48, or many more than two trabecular fibers 48. In addition, for brevity and clarity of illustration, all embodiments herein are shown with a single anchoring device (e.g. the first portion 42 and the fixation device 46) for the substrate portion where the trabecular fibers 48 may form (e.g. the second portion 44). However, it is understood that embodiments may include additional substrate portions and fixation devices as desired to secure the substrate portion where the trabecular fibers 48 may form.

FIGS. 3A-3C are schematic cross-sectional views illustrating exemplary cross-sectional shapes for the second portion 44 of the substrate 40. In some embodiments, the second portion 44 may have an elliptical cross-sectional shape as shown in FIG. 3A. A circular cross-sectional shape is also envisioned, as that is a type of elliptical shape. In other embodiments, the second portion 44 may have a rectangular cross-sectional shape, as shown in FIG. 3B. A square cross-sectional shape is also envisioned, as that is a type of rectangular shape. In still other embodiments, the second portion 44 may have a triangular cross-section as shown in FIG. 3C.

Figure 4:
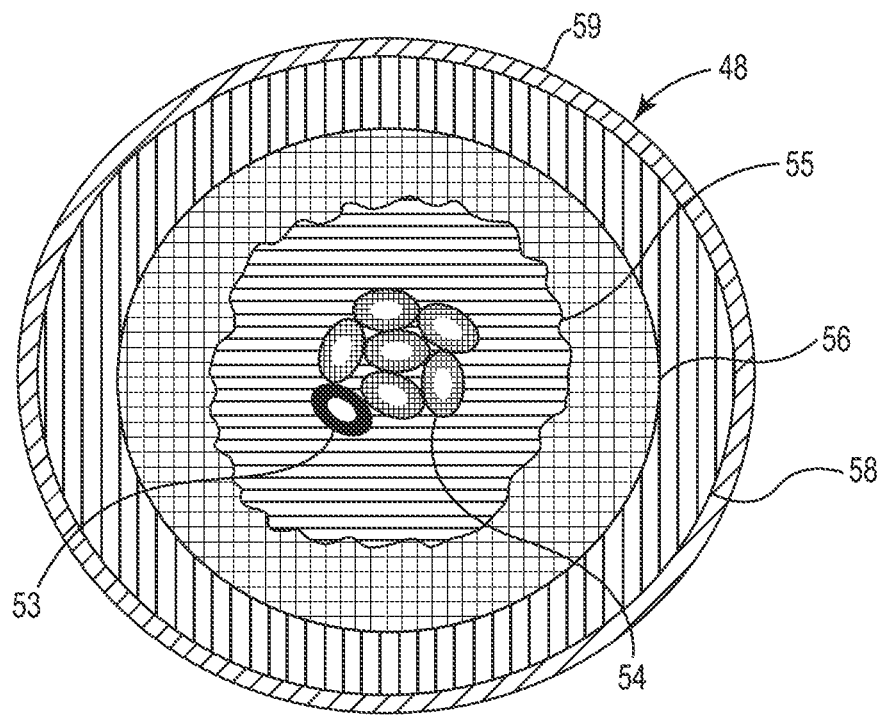
FIG. 4 is a schematic cross-sectional view of a trabecular fiber containing cardiomyocyte cells.

FIG. 4 is a schematic cross-sectional view of the trabecular fiber 48. In the particular illustrated embodiment, the trabecular fiber 48 may include a blood vessel 53, a plurality of cardiomyocyte cells 54, an extracellular matrix layer 55, an elastin layer 56, an outer collagen layer 58, and an endothelial cell layer 59. The cardiomyocyte cells 54 may be disposed at a core of the trabecular fiber 48 and may be generally oriented with their long-axis (not shown) parallel to the long-axis of the trabecular fiber 48 (shown in FIG. 2). The cardiomyocyte cells 54 may be embedded in an extracellular matrix formed by the extracellular matrix layer 55, and may be nourished by the blood vessel 53 coursing in parallel to the cardiomyocyte cells 54. The outer collagen layer 58 may be an external layer of the trabecular fiber 48. The elastin layer 56 may be disposed between the extracellular matrix layer 55 and the outer collagen layer 58. Although the trabecular fiber 48 layers are illustrated with distinct boundaries, it is understood that there may be mixing of the layers at their respective interfaces. The overall organizational histologic architecture of the trabecular fiber 48 is that of a tube (the cardiomyocyte cells 54), within a tube (the elastin layer 56), within a tube (the outer collagen layer 58). The presence of the cardiomyocyte cells 54 at the core of the trabecular fiber 48 distinguishes the trabecular fiber 48 from structures of similar appearance, such as chordae tendineae of the tricuspid valve 18 (FIG. 1). Without wishing to be bound by any theory, it is believed that the presence of the substrate 44 in the dynamic environment of the right ventricle 14 produces mechanical stresses on the endocardium 38 and the heart 12. It is believed that these stresses stimulate the growth of the trabecular fiber 48 including the core of cardiomyocyte cells 54.

Figure 5:
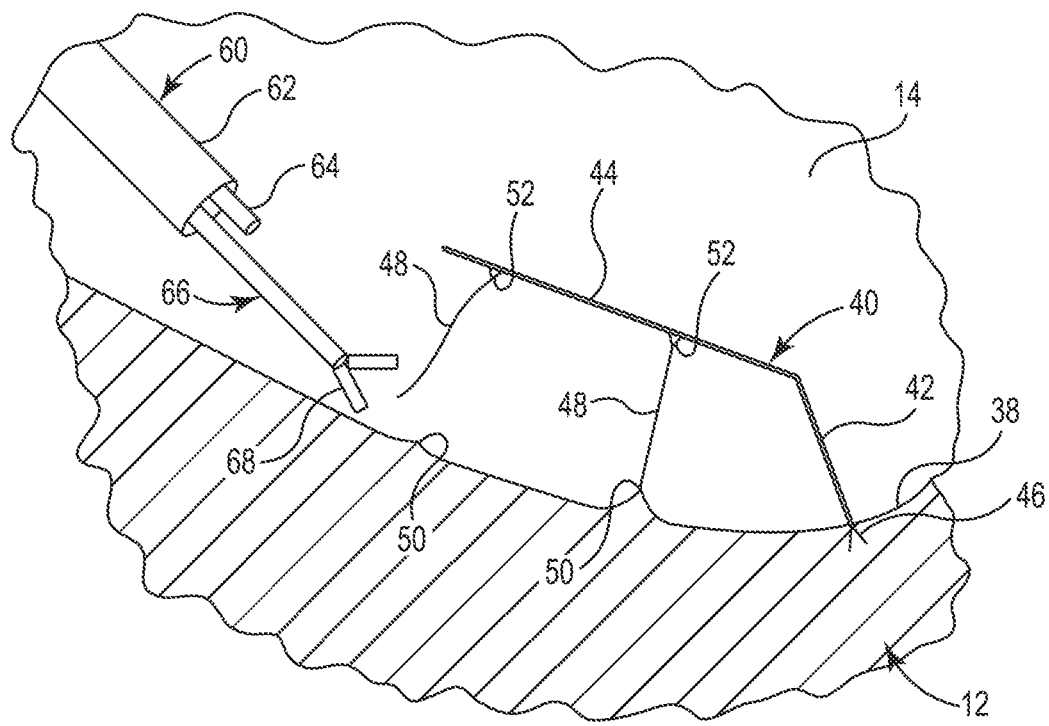
FIGS. 5-6 are schematic views illustrating a method of harvesting the trabecular fibers 48 shown in FIG. 2 in accordance with embodiments of the present invention.
Figure 6:
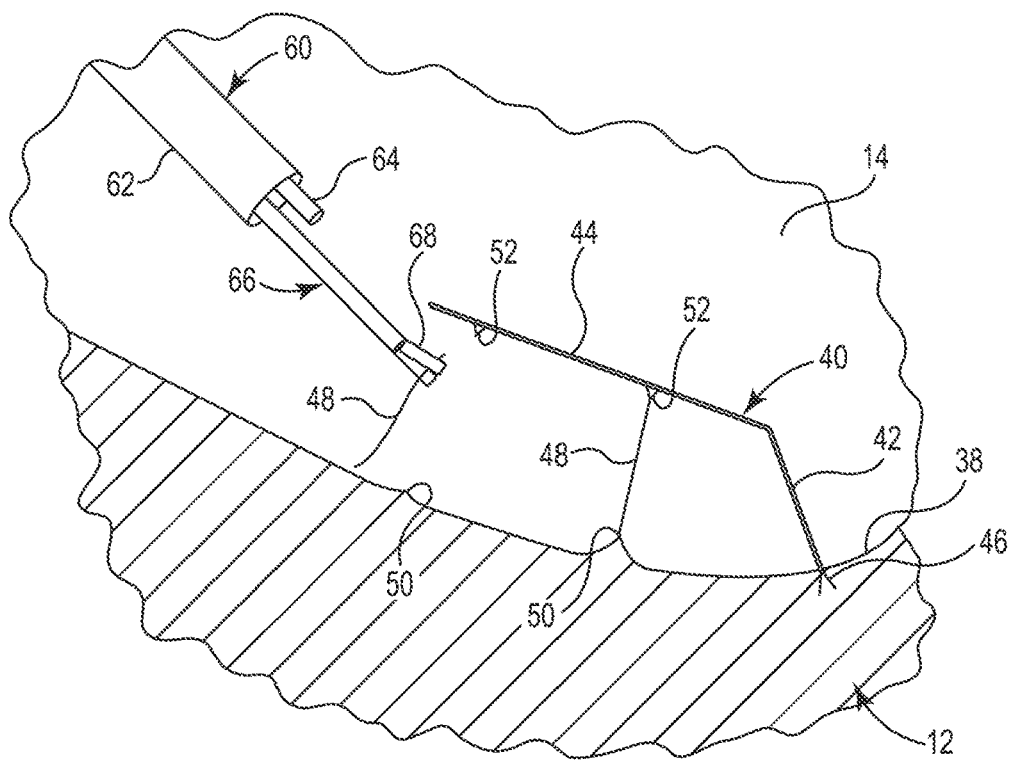

FIGS. 5-6 are schematic views illustrating a method of harvesting the trabecular fibers 48 shown in FIG. 2 in accordance with embodiments of the present invention. FIGS. 5 and 6 show a tool 60 for imaging and extracting the trabecular fibers 48. The tool 60 may include a catheter 62, a visualization device 64, and a forceps device 66. The forceps device 66 may include a pair of jaws 68. The pair of jaws 68 may be used to cut and/or grasp tissue, such as the trabecular fiber 48. The catheter 62 may include a plurality of lumens (not shown) extending the length of the catheter 62 for accommodating the visualization device 64 and the forceps device 66. The catheter 62 may be maneuvered into the right ventricle 14 as described above for catheter 30 in reference to FIG. 1.

In some embodiments, the catheter 62 may be, for example, a SpyGlass® Catheter from Boston Scientific Corporation, Natick, Massachusetts. In some embodiments, the visualization device 64 may be a fiber-optic based device, for example, a SpyGlass® Direct Visualization Probe from Boston Scientific Corporation, Natick, Massachusetts. In other embodiments, the visualization device 64 may include a solid-state camera, a transparent balloon (not shown) extending around the camera, and a source of saline (not shown) for inflating the transparent balloon to enhance direct visualization by displacing blood proximate to the substrate 40 and the trabecular fiber 48. In some embodiments, the forceps device 66 may be, for example, a SpyBite® Biopsy Forceps from Boston Scientific Corporation, Natick, Massachusetts. In some embodiments, the tool 60 may further include a separate light source (not shown).

As shown in FIG. 5, harvesting the trabecular fiber 48 may include cutting away the trabecular fiber 48 from the endocardium 38 by operation of the pair of jaws 68 of the forceps device 66. In some embodiments, the trabecular fiber 48 may be cut away from the endocardium 38 at the location 50 where the trabecular fiber 48 extends from the endocardium 38. As shown in FIG. 6, harvesting the trabecular fiber 48 may include cutting away the trabecular fiber 48 from the substrate 40 by operation of the pair of jaws 68 of the forceps device 66. In some embodiments, the trabecular fiber 48 may be cut away from the substrate 40 at the location 52 where the trabecular fiber 48 extends from the substrate 40. As shown in FIG. 6, once the trabecular fiber 48 is cut away from both the endocardium 38 and the substrate 40, the pair of jaws 68 may grasp the trabecular fiber 48. The forceps device 66 may be withdrawn through the lumen in the catheter 62 to remove the entire trabecular fiber 48 from the heart 12 for beneficial uses as described above. The process may be repeated for harvesting multiple trabecular fibers 48. Although the process is illustrated as cutting away the trabecular fiber 48 from the endocardium 38, and then cutting away the trabecular fiber 48 from the substrate 40, it is understood that embodiments may include cutting away the trabecular fiber 48 from the substrate 40, and then cutting away the trabecular fiber 48 from the endocardium 38.

Once the trabecular fibers 48 have been harvested, the forceps device 66 may be used to grasp the substrate 40, detach the substrate 40 from the endocardium 38, and remove the substrate 40 from the heart 12. Alternatively, the substrate 40 may be maintained in contact with the endocardium 38 for a time at least sufficient for the formation of additional trabecular fibers 48 for future harvesting.

Figure 7:
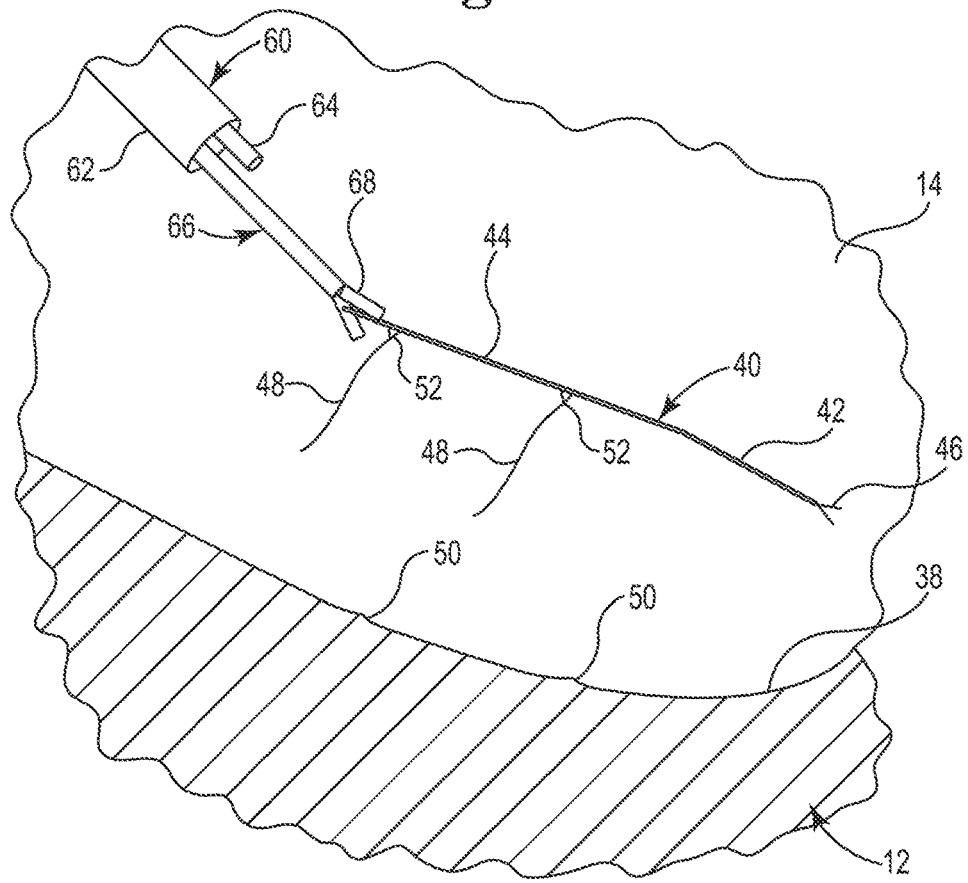
FIG. 7 is a schematic view illustrating another method of harvesting the trabecular fibers 48 shown in FIG. 2 in accordance with embodiments of the present invention.

FIG. 7 is a schematic view illustrating another method of harvesting the trabecular fibers 48 shown in FIG. 2 in accordance with embodiments of the present invention. As shown in FIG. 7, harvesting the trabecular fiber 48 may include cutting away the trabecular fiber 48 from the endocardium 38 by operation of the pair of jaws 68 of the forceps device 66. In some embodiments, the trabecular fiber 48 may be cut away from the endocardium 38 at the location 50 where the trabecular fiber 48 extends from the endocardium 38. The cutting away of the trabecular fibers 48 from the endocardium 38 may be repeated until all of the trabecular fibers 48 to be harvested are severed from the endocardium 38. Once the trabecular fibers 48 have been severed from the endocardium 38, the forceps device 66 may be used to grasp the substrate 40, detach the substrate 40 from the endocardium 38, and remove the substrate 40 from the heart 12 with the trabecular fiber 48 still attached to the substrate 40. The trabecular fiber 48 may be cut away from the substrate 40 after the substrate 40 is removed from the heart 12.

Figure 8:
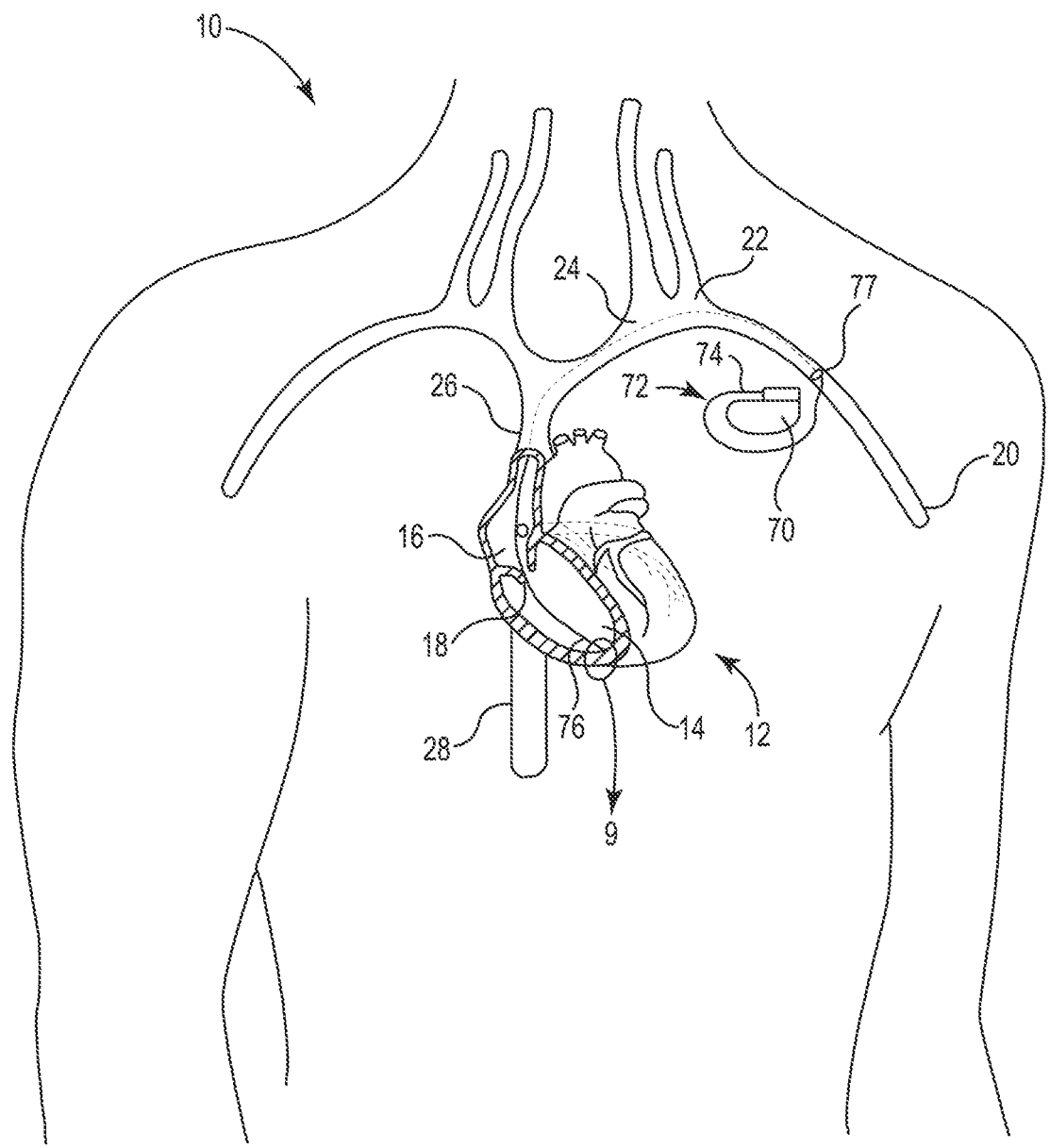
FIG. 8 is a schematic view illustrating the implantation of a substrate for stimulating the growth of new contractile heart muscle tissue, or cardiomyocyte cells, in accordance with embodiments of the present invention.

FIG. 8 is a schematic view illustrating the implantation of a substrate for stimulating the growth of new contractile heart muscle tissue, or cardiomyocyte cells, in accordance with embodiments of the present invention. FIG. 8 shows a voltage generator 70 and a stimulation lead 72. The voltage generator 70 may be subcutaneously implanted within the patient 10. The voltage generator 70 may be battery-powered and may produce an electrical potential in the form of a series of electrical pulses and/or in the form of a continuous electrical potential. The stimulation lead 72 may include a proximal end 74 and a distal end 76. The stimulation lead 72 may be physically and electrically connected to the voltage generator 70 at the proximal end 74. In some embodiments, the stimulation lead 72 may enter the left auxiliary vein 20 through a vascular entry site 77. The distal end 76 may be maneuvered through a left auxiliary vein 20, the left subclavian vein 22, the left brachiocephalic vein 24, the superior vena cava 26, and into the heart 12 at the right atrium 16. The distal end 76 may be maneuvered from the right atrium 16, through the tricuspid valve 18, and into the right ventricle 14. The stimulation lead 72 may include at least one lumen (not shown) extending from the proximal end 74 to the distal end 76 through which instruments (not shown) may be used to implant a substrate into the endocardium 38 lining the walls of the right ventricle 14, such as a substrate 78 for stimulating the growth of new cardiomyocyte cells as described below in reference to FIG. 9. The stimulation lead 72 may also include at least one lumen (not shown) extending from the proximal end 74 to the distal end 76 through which an electrical conductor (not shown) may pass to electrically connect the voltage generator 70 to an electrode at the distal end 76, such as an electrode 84 of the substrate 78, as described below in reference to FIG. 9. In this way, the voltage generator 70 may produce an electrical potential between the electrode 84 and the heart 12.

Figure 9:
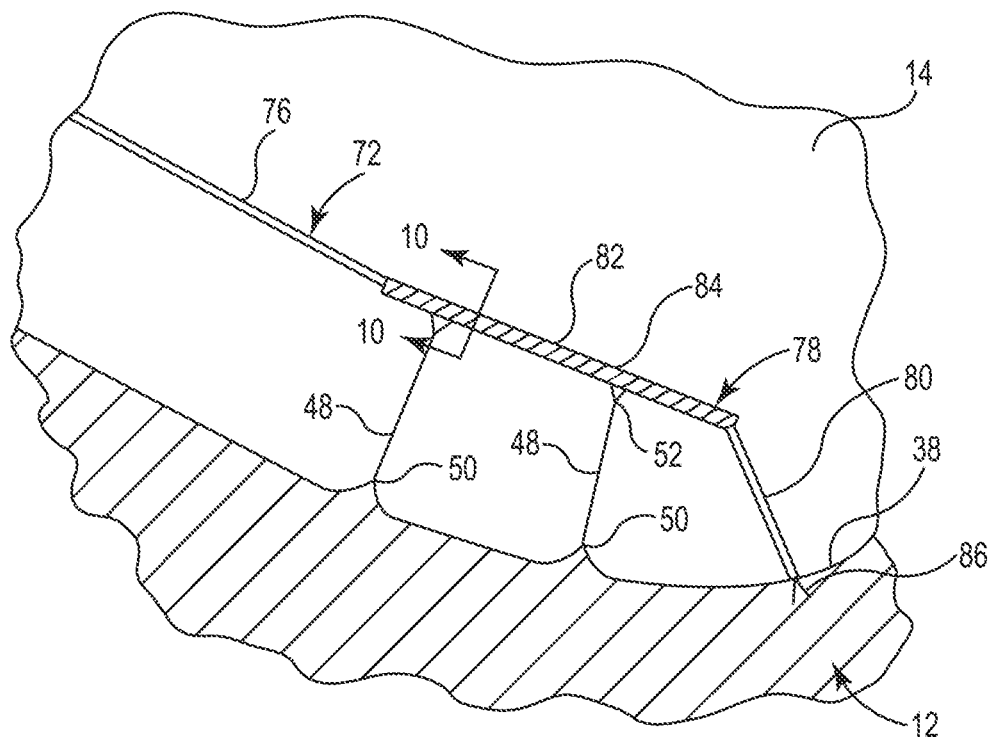
FIG. 9 is a schematic view of a portion of the patient's heart further illustrating implanted substrate of FIG. 8.

FIG. 9 is a schematic view illustrating the substrate 78 implanted into the endocardium 38 of the heart 12. FIG. 9 shows the substrate 78 includes a first portion 80, a second portion 82, the electrode 84, and a fixation device 86. The substrate 78 may be made of a biocompatible polymer, for example, a polyurethane polymer, a polyether ether ketone polymer, a silicone polymer, a styrene-isobutylene-styrene block copolymer, or an expanded polytetrafluoroethylene polymer. Alternatively, the substrate 78 may be made of an organic substance, for example, cellulose, fibrin, fibrinogen, or fibronectin. The substrate 78 may be a solid or an e-spun mesh. The fixation device 86 may be as described above for the fixation device 46 in reference to FIG. 2. The fixation device 86 may be connected to one end of the first portion 80 to anchor the substrate 78 to the endocardium 38. In some embodiments, the electrode 84 may be made of a biocompatible electrical conductor, for example, platinum, platinum-iridium alloy, iridium, iridium oxide, titanium, titanium nitride, tantalum, or platinum black. In some embodiments, the electrode 84 may cover at least a portion of an external surface of the second portion 82 as described below in reference to FIG. 10. The second portion 82 may be connected to the other end of the first portion 80 and may not be in contact with the endocardium 38. That is, the second portion 82 and the electrode 84 may be spaced apart from the endocardium 38. The electrode 84 may be electrically connected to the voltage generator 70 by way of the electrical conductor within the stimulation lead 72, as described above in reference to FIG. 8.

The substrate 78 may be maintained within the heart 12 for a time at least sufficient for the formation of the trabecular fiber 48 extending between the endocardium 38 and the second portion 82, as shown in FIG. 9. Maintaining the substrate 78 may include anchoring the substrate 78 to the endocardium 38 with the fixation device 86. Maintaining the substrate 78 may also include producing an electrical potential between the electrode 84 and the endocardium 38. Without being bound by any theory, it is believed that the electrical potential between the endocardium 38 and the electrode 84 may further stimulate the growth of the trabecular fibers 48 containing cardiomyocyte cells 54 (FIG. 4). In some embodiments, the trabecular fiber 48 may extend from the endocardium 38 at a location 50. In some embodiments, the endocardium 38 may be pulled toward the second portion 82 due to tension transmitted along the trabecular fiber 48 between the endocardium 38 and the substrate 78. In some embodiments, the trabecular fiber 48 may extend from the substrate 78 at a location 52.

Figure 10:
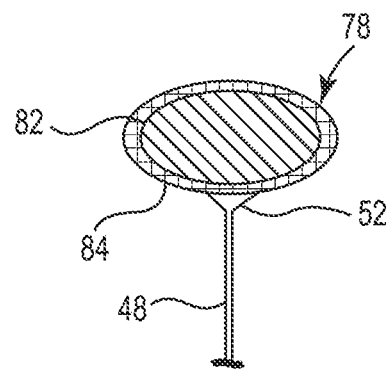
FIG. 10 is a schematic cross-sectional view the substrate of FIG. 9.

FIG. 10 is a schematic cross-sectional view of the second portion 82 of the substrate 78. As shown in FIG. 10, in some embodiments the electrode 84 may axially surround the second portion 82. In other embodiments, the electrode 84 may cover only a side of the second portion 82 facing the endocardium 38 (FIG. 9). Although the second portion 82 is shown with an elliptical cross-sectional shape, embodiments may include other cross-sectional shapes including those described above for second portion 44 in reference to FIGS. 3A-3C.

The embodiment shown in FIGS. 8-10 includes the voltage generator 70 subcutaneously implanted and connected to the electrode 84 of the substrate 78 by the stimulation lead 72. It is understood that embodiments also include leadless configurations in which the voltage generator 70 may be implanted within the heart along with the substrate 78, and directly connected to the substrate 78 without the need for stimulation lead 72.

The embodiment of FIGS. 9-10 is shown with the electrode 84 as a single, contiguous electrode covering at least a portion the external surface of the second portion 82. However, it is understood that embodiments may include a plurality of separate electrodes 84 covering at least a portion of the second portion 82, and the formation of the trabecular fibers 48 extending between the endocardium 38 and each of the separate electrodes 84.

Figure 11:
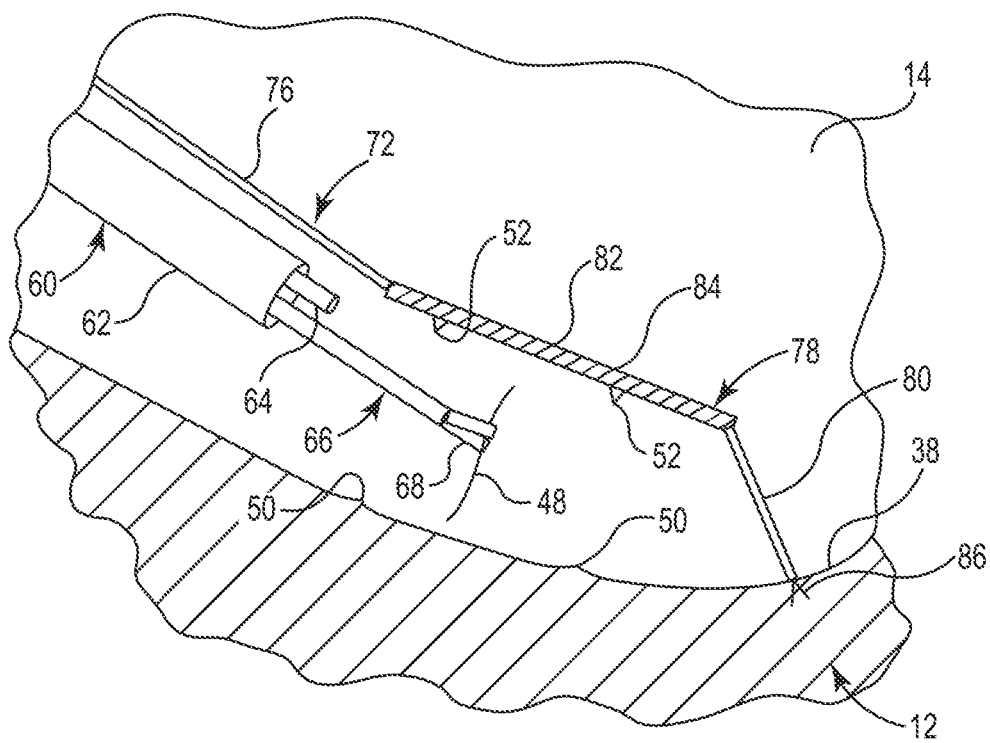
FIGS. 11-12 are schematic views of a portion of the patient's heart further illustrating methods of harvesting the trabecular fibers shown in FIG. 9 in accordance with embodiments of the present invention.
Figure 12:
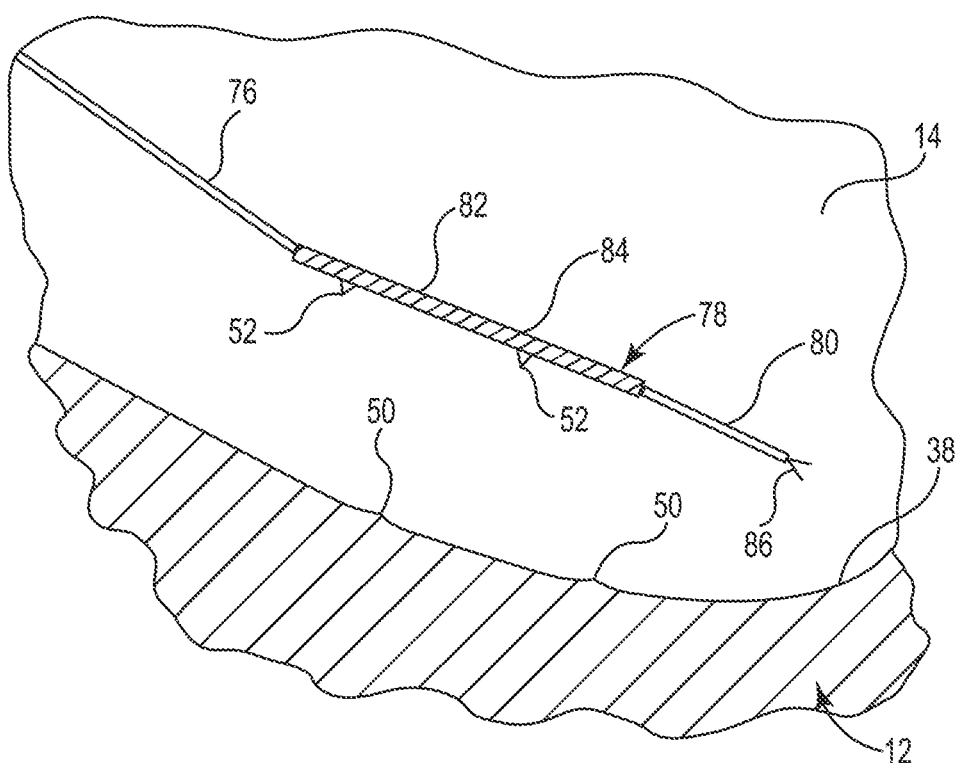

FIGS. 11-12 are schematic views illustrating a method of harvesting the trabecular fibers 48 shown in FIG. 9 in accordance with embodiments of the present invention. The tool 60 may harvest the trabecular fiber 48 by cutting away the trabecular fiber 48 from the endocardium 38 and from the electrode 84. In some embodiments, the trabecular fiber 48 may be cut away from the endocardium 38 at the location 50 where the trabecular fiber 48 extends from the endocardium 38. In some embodiments, the trabecular fiber 48 may be cut away from the electrode 84 at the location 52 where the trabecular fiber 48 extends from the electrode 84. As shown in FIG. 6, once the trabecular fiber 48 is cut away from both the endocardium 38 and the electrode 84, the pair of jaws 68 may grasp the trabecular fiber 48. The forceps device 66 may be withdrawn through the lumen in the catheter 62 to remove the trabecular fiber 48 from the heart 12 for beneficial uses as described above in reference to FIG. 5. The process may be repeated for harvesting multiple trabecular fibers 48.

Once the trabecular fibers 48 have been harvested, tension may be applied to the stimulation lead 72 to dislodge the fixation device 86 from the endocardium and remove the substrate 78 from the heart 12. Alternatively, the substrate 78 may be maintained in contact with the endocardium 38 for a time at least sufficient for the formation of additional trabecular fibers 48 for future harvesting.

Embodiments above are shown cutting the trabecular fiber 48 in a way to harvest as much of the trabecular fiber 48 as possible. However, it is understood that embodiments include methods that harvest only a sub-segment of the trabecular fiber 48 by, for example, cutting the trabecular fiber 48 away from the endocardium 38 at a distance from the endocardium 38, rather than at the location 50 as shown in FIGS. 5-7, 9, and 11-12.

In the interest of brevity, embodiments above are described with the substrate implanted within the right ventricle of the heart. However, it is understood that the present invention encompasses embodiments having the substrate implanted within the left ventricle of the heart as well.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for producing cardiomyocyte cells comprising:
   positioning a substrate including an electrode within a heart such that the substrate is in physical contact with an endocardium, and the electrode is not in physical contact with the endocardium;
   maintaining the substrate within the heart for a time at least sufficient to form trabecular fibers extending between the endocardium and the electrode, wherein the trabecular fibers contain cardiomyocyte cells;
   removing the trabecular fibers from the heart.

2. The method of claim 1, wherein maintaining includes:
   anchoring the substrate to the endocardium with a fixation device; and
   producing an electrical potential between the electrode and the endocardium.

3. The method of claim 2, wherein the electrical potential is produced as a series of electrical pulses.

4. The method of claim 2, wherein the electrical potential is produced continuously.

5. The method of claim 1, wherein the substrate includes a biocompatible polymer and the electrode includes a biocompatible electrical conductor.

6. A method of harvesting cardiomyocyte cells comprising:
   forming trabecular fibers extending between an endocardium and a substrate, wherein the substrate is positioned within a heart, and wherein the trabecular fibers contain cardiomyocyte cells;
   cutting away the trabecular fibers from the endocardium;
   cutting away the trabecular fibers from the substrate; and
   removing the trabecular fibers from the heart.

7. The method of claim 6, wherein the trabecular fibers are cut from the endocardium at a location where the trabecular fibers extend from the endocardium.

8. The method of claim 6, wherein the trabecular fibers are cut from the substrate at a location where the trabecular fibers extend from the substrate.

9. The method of claim 6, further including removing the substrate from the heart after removing the trabecular fibers containing the cardiomyocyte cells from the heart.

\* \* \* \* \*